United States Patent [19]
Rothwell et al.

[11] Patent Number: 6,090,775
[45] Date of Patent: Jul. 18, 2000

[54] TREATMENT OF NEUROLOGICAL CONDITIONS BY AN INTERLEUKIN-1 INHIBITING COMPOUND

[75] Inventors: Nancy Jane Rothwell, Poulton-le-Fylde; Gareth Roberts, London, both of United Kingdom

[73] Assignee: The Victoria University of Manchester, Manchester, United Kingdom

[21] Appl. No.: 08/232,167

[22] PCT Filed: Nov. 2, 1992

[86] PCT No.: PCT/GB92/02023

§ 371 Date: Jul. 29, 1994

§ 102(e) Date: Jul. 29, 1994

[87] PCT Pub. No.: WO93/08820

PCT Pub. Date: May 13, 1993

[30] Foreign Application Priority Data

Oct. 31, 1991 [GB] United Kingdom .................... 9123161
Nov. 30, 1991 [GB] United Kingdom .................... 9125670

[51] Int. Cl.$^7$ ............................ A61K 38/00; A61K 38/20
[52] U.S. Cl. ................................ 514/2; 514/12; 424/85.2; 530/350; 530/351
[58] Field of Search .......................... 514/2, 12; 530/350, 530/351; 424/85.2

[56] References Cited

PUBLICATIONS

Rudinger In "Peptide Hormones" (Jun. 1976) ed. J.A. Parsons, University Park Press, Baltimore, pp. 1–7.

Lieberman, International Rev. of Neurobiology 14 (1971) 49–124.

Jackowski, British J. of Neurosurgery 9 (1995) 303–317.

Hefti et al., Neurobiol. of Aging 9 (1988) 689–690.

Marx, Science 255 (1992) 688–689.

Meldrum et al. TIPS 11 (1990) 379–387.

The Merck Manual—14th edition (1982) p. 1414.

Guenard et al J. Neurosci. Bes. 29 396–400 (1991).

Relton et al J. Physiol. 452 122P (1992).

Relton et al Brain Res. Bull 29 243–246 (1992).

Jacobs et al J. Immunol. 146 2983–9 (1991).

Stockman et al Biochemistry 31 5237–45 (1992).

Dana Giulian, et al., "Interleukin 1 of the central nervous system is produced by ameboid microglia", J. Exp. Med. The Rockerfeller University Press. vol. 164, Aug. 986, pp. 594–604.

Dmitry Goldgaber, et al., "Interleukin 1 regulates synthesis of amyloid β–protein precursor mRNA in human endothelial cells", Proc. Natl. Acad. Sci. USA. vol. 86, pp. 7606–7610, Oct. 1989.

W. Sue T. Griffin, et al., "Brain interleukin 1 and S-100 immunoreactivity are elevated in Down syndrome and Alzheimer disease", Proc. Natl. Acad. Sci. USA, vol. 86, pp. 7611–7615, Oct. 1989.

Masabumi Minami, et al., "Convulsants induce interleukin 1β messenger RNA in rat brain", Biochemical and Biophysical research communications, vol. 171, No. 2, 1990, Sep. 14, 1990, pp. 832–837.

Jane K. Relton, et al., "Lipocorin–1 is an endogenous inhibitor of ischemic damage in the rat brain", J. Exp. Med The Rockerfeller University Press, vol. 174, Aug. 1991, pp. 305–310.

Nancy Jane Rothwell, "Functions and mechanisms of interleukin 1 in the brain", Elsevier Science Publishers Ltd. vol. 12, Nov. 1991, pp. 430–436.

Dana Giulian, et al., "Interleukin–1 injected into mammalian brain stimulates astrogliosis and Neovascularization", The Journal of Neuroscience, Jul. 1988, 8(7) 2485–2490.

International Search Report, Pat. Appl. No. PCT/GB92/02023, Mar. 5, 1993.

A. Lachaux, "Les antagonistes du recepteur de L'interleukine–1", Pediatrie, vol. 46, No. 10, 1991, p.

D. B. Carter, "Purification, cloning, expression and biological characterization of an interleukin–1 receptor antagonist protein", Nature, vol. 344, Apr. 12, 1990, pp. 633–637.

F. Carey, et al., "Lipocortin 1 fragment modifies pyrogenic actions of cytokines in rats", American Physiological Society, 1990.

Jane K. Relton, et al., "Lipocortin–1 is an Endogenous Inhibitor is Ischemic Damage in the Rat Brain", J. Exp. Med. The Rokefeller University Press, vol. 174, Aug. 1991.

Charles H. Hannum, et al., "Interleukin–1 receptor antagonist activity of a human interleukin–1 inhibitor", Nature, vol. 343, Jan. 25, 1990.

Stephen P. Eisenberg, et al., "Primary structure an functional expression from complementary DNA of a human interleukin–1 receptor antagonist", Nature, vol. 343, Jan. 25, 1990.

*Primary Examiner*—Anthony C. Caputa
*Assistant Examiner*—Robert C. Hayes
*Attorney, Agent, or Firm*—Akin, Gump, Strauss, Hauer & Feld, LLP

[57] ABSTRACT

The use of a compound which prevents, inhibits or modifies the action of interleukin-1 as an active agent for the treatment of conditions of neurological degeneration. The active agent may be IL-1 receptor antagonist, particularly recombinant IL-1 ra.

22 Claims, 2 Drawing Sheets

TREATMENT OF NEUROLOGICAL CONDITIONS BY AN INTERLEUKIN-1 INHIBITING COMPOUND

FIELD OF THE INVENTION

This invention relates to a method for treatment of neurological conditions and to compositions and products useful for such treatment.

BACKGROUND OF THE INVENTION

Neurological conditions pose serious clinical problems, as their effects are severe and long-lasting but little is known of any really effective means for curing or even controlling them.

There is, therefore, a considerable need for some treatment for such conditions.

SUMMARY OF THE PREFERRED EMBODIMENTS

According to a first aspect of the present invention there is provided the use of a compound which prevents, inhibits or modifies the action of interleukin-1 as an active agent for the treatment of conditions of neurological degeneration.

According to a second aspect of the present invention there is provided a formulation adapted for the use as defined in the previous paragraph, comprising an active agent as defined therein dispersed or dissolved in a pharmaceutically acceptable carrier (solvent or diluent), especially in water or an aqueous medium, especially in normal saline (an isotonic solution of sodium chloride in water).

According to a third aspect of the present invention there is provided a method of treating neurological degenerative conditions in a human or animal patient comprising administration as an active agent a compound which prevents, inhibits or modifies the action of interleukin-1.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

DETAILED DESCRIPTION OF PREFERRED EMBODIMENTS

Figure 1:
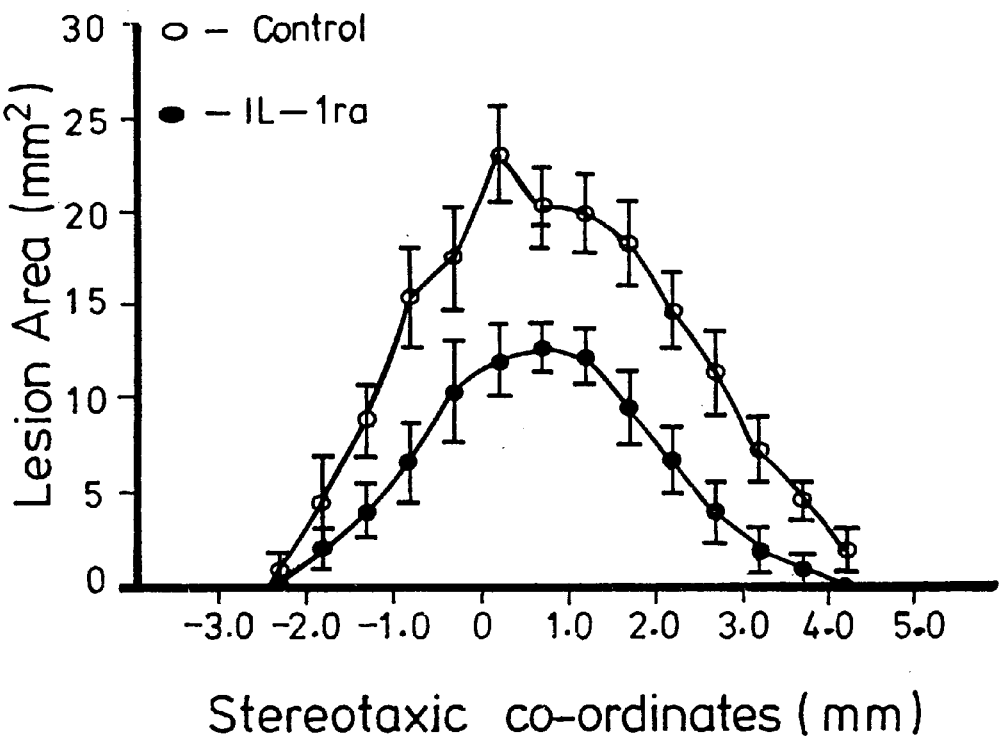
FIGS. 1A–B illustrate the effect of IL-1 receptor antagonist protein (IL-1 ra) on neuronal damage after cerebral ischemia. (B) The lower panel shows the volume of damage ($mm^3$, computed from the volume under the curve for upper panel, A). Mean±SEM, one way ANOVA, *$P<0.05$.
Figure 1:
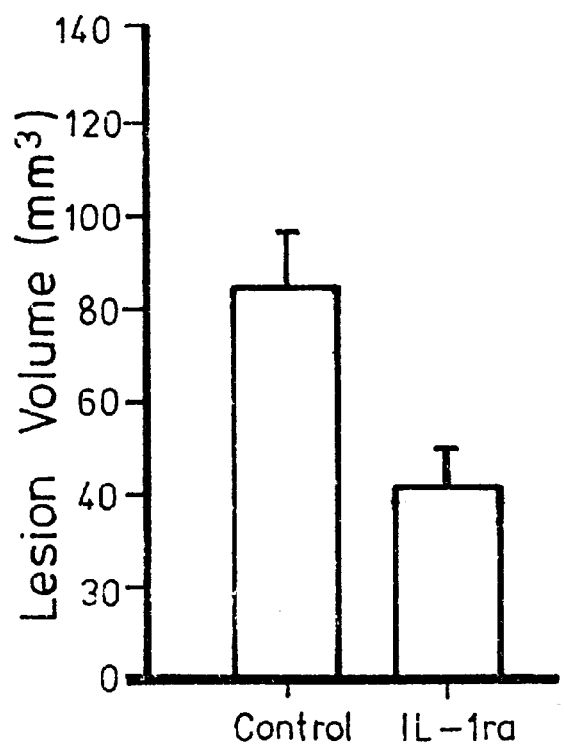

Interleukin-1 is commonly referred to as "IL-1".

The active agent thus defined has the effect of protecting neurons from adverse effects, i.e. neuro-degeneration.

The active agent used may be in a variety of forms, for example a naturally occurring product or one produced by artificial or synthetic methods, for example a genetically engineered form. Particularly suitable is interleukin-1 receptor antagonist protein (conveniently referred to as "IL-1ra"), particularly recombinant IL-1 ra. It is also possible to use analogues of IL-1 ra, as well as derivatives and fragments thereof (and analogues of these compounds).

Our treatment is useful for a variety of conditions of neurological degeneration, however caused, though the means by which the active agent we specify here works is not yet clearly understood. It is believed that it is probably by blocking the action of interleukin-1. The invention is especially applicable to treatment of the neurons in the brain, periphery and spinal chord.

Cerebral lesions in several chronic neurodegenerative conditions (e.g. Alzheimer's disease (AD) and Down's Syndrome) are known to be associated with the formation of beta-amyloid (beta-AP), apparently due to abnormal metabolism of beta-amyloid precursor protein (beta-APP) with consequent deposition of beta-AP.

IL-1 has been demonstrated to be present in the brains of patients with Down's Syndrome and Alzheimer's Disease (Griffin et al, 1989, Proc Nat Acad Sci 86, 7611) and in separate studies has been shown to induce synthesis of the precursor of beta-APP (Goldberg et al, 1989, Proc Nat Acad Sci 86, 7606).

Furthermore chronic degenerative processes associated with over-expression of beta-APP for an extended period can lead to loss of synapses, deposition of beta-AP and degeneration of neurons. We have shown that this process is related to emergence of the clinical symptoms of cognitive and neurological deficits and demention (Gentleman S. M. et al. (1991). Neuropath.Applied Neurobiol.17,531). Our experimental data show that these mechanisms are probably active in many of the diseases described in Chapters 5 and 6 of the International Classification of Disease (10th edition) (e.g. Dementia in Alzheimer's disease, Parkinson's Disease, Cortical Lewy Body Disease, etc.)

Interleukin-1 (IL-1), a 17 KDa cytokine is synthesised (W. L. Farrar et al., Immunol.Rev. 100, 361, 1981) and acts within the central nervous system to mediate several aspects of the acute phase response, and directly modifies neuronal and glial function. An endogenous IL-1 receptor antagonist (IL-1ra) has been identified (S. P. Eisenberg et al., Nature, 343, 341, 1990) which binds to IL-1 receptors in peripheral tissues and hippocampal neurones, and has been shown to inhibit many peripheral actions of IL-1.

Further evidence that IL-1ra may be of benefit derives from observations that the concentrations of IL-1 and related cytokines are increased in brain in response to traumatic injury, cerebral ischaemia, and HIV infection and administration of IL-1 worsens ischaemic brain damage. (Gentleman et al (1993) Prog. Exp. Brain Res.(in press)) Thus, blocking its actions by administration of IL-1ra or related inhibitors of IL-1 action may limit many forms of neurological damage.

The molecular weight of the active agent defined herein may vary over a considerable range. It may thus usually be of molecular weight up to about 40 KDa (kilodaltons)— though products of higher or lower molecular weight may be used if desired—and preferably in the range 5 to 25 KDa; especially in the range 15 to 20 KDa. Commonly, products of molecular weight about 17 KDa are convenient and accessible.

The active agents may be administered by various modes, conventional in the art, and the choice depends upon what may be considered most appropriate for the patient's condition. Thus they may be introduced directly into the site of an identified or suspected neuro-degeneration, taking appropriate care that the administration does not itself cause undue damage to the tissue or affect the condition adversely. This may be done by injection, e.g. central injection, (for example stereotaxic injection) via hypodermic needles, cannulae, or the like. For intra-cranial administration pump-assisted apparatus may be used.

Alternatively, they may be administered by indirect methods, so that they then migrate within the body from the site of introduction to the site at which they are required and are to have effect. Thus, administration by infusion can be used, and this can be preferred when direct access to the site of action is either difficult or considered to be less desirable, or even may not be easily determinable. The mode by which this migration occurs may vary, and may be for example by transfer through the blood stream or the cerebro-spinal fluid. Thus, the active agent may be administered by introduction at a peripheral site, for example by intravenous infusion.

So, for the treatment of brain conditions, the invention gives the user a considerable choice, as administration may be by direct injection into the intra-cranial cavity, by infusion into the intra-cranial cavity, conveniently by way of the cerebro-spinal fluid, or by introduction at a peripheral site, for example by intravenous infusion.

Combinations of more than one administration technique may be used if desired.

Administration may be achieved by conventional apparatus. Furthermore the active agent may be administered in conjunction with other known treatment agents and/or procedures.

The formulations used may be any in which the defined compound (active agent) is contained in a medium which is safe and compatible with the tissues into which it is to be introduced. Thus the compound may be dispersed or dissolved in a pharmaceutically acceptable carrier (solvent or diluent). This is most conveniently water or an aqueous medium—especially normal saline (an isotonic solution of sodium chloride in water)—though other media may be used if desired provided they are pharmaceutically acceptable and compatible with the area to be treated. Thus, conventional adjuvants and additives may be used, for example in normal saline.

The amount and concentration of the active agent appropriate for administration may be varied according to the particular need of the patient and the type and/or severity of the condition to be treated. The amount of the active agent is most suitably (for injection into the site of damage) in the range 100 to 10,000 micrograms (and preferably in the range 1000 to 5000 micrograms), on the basis of a patient of 80 kg body weight, and an amount of about 2400 micrograms is usually typical and convenient, though larger or smaller amounts may be used if desired.

If it is considered more convenient, these amounts can be converted into "micrograms per kilogram of body weight" figures by simple calculation, and expressed in this way so that the dosages can be calculated more readily for various patients.

These amounts are those which it is intended should be at the site at which the agent is to act. Thus, if the agent is not introduced directly into the desired site, the amounts required for indirect introduction (e.g. by infusion from a peripheral site) should be adjusted so as to give the amount stated above at the site of action. In such cases, the amount used at the peripheral site will usually need to be greater than in the ranges stated above, but the optimum amount in any individual case may be determined by clinical factors, having regard to factors as the patient's condition and the response to the treatment. For example, a relatively high dosage may be most appropriate for a condition of acute trauma or at the commencement of treatment, while a lower or reduced dosage may be most appropriate for a chronic or continuing condition calling for an extended period of treatment.

The mode of treatment may be varied to suit the condition being treated. Thus, for example, a single adminstration may suffice in some cases to provide the desired protection rapidly in acute conditions, but this may be enhanced by continuing administration, while chronic conditions may need continuous administration. The optimum mode and dosage for any particular patient or condition can thus be determined by simple trial, and can be modified as treatment continues, in the light of the results shown by the patient's response and needs.

The treatment of the present invention may be applied to a variety of acute and chronic conditions.

Our invention may be applicable to the treatment of relatively long-term neuro-degeneration of non-ischaemic origin (e.g. epilepsy, Alzheimers disease, Huntingdon's chorea, Downs syndrome, Multiple Sclerosis and Parkinson's disease) and neurological damage resulting from chronic infection for example HIV producing the syndrome of AIDS.

It may also be used for the treatment of ischaemic conditions, for example cerebral ischaemia (stroke, haemorrhage or brain injury as a result of trauma) which involve various forms of brain damage and may lead to acute or delayed damage to the brain neurons, and to degeneration—for example after head trauma.

The time of treatment is also significant and can be important. Administration may be before or after an ischaemic condition has occurred or is suspected. Administration before an ischaemic condition can be of value for prophylactic treatment, for example when the patient or subject is considered to be at risk of an ischaemic condition. Such conditions could be for example be in cardiac bypass surgery, in which a significant proportion of patients can suffer minor cerebral damage, or in childbirth, in which the foetus may be liable to problems in the foetal circulation potentially leading to anoxia and cerebral palsy and the like. The more common time of administration is after ischaemic damage has occurred or is suspected, for example in the conditions of treating a stroke or a head injury, and in such cases it is desirable to make the administration as soon as possible after the event to get best results—preferably within an hour or less, though administration later than that time may still be beneficial.

The efficacy of our invention is illustrated by the ability of treatment by administration of active agents we now specify herein to reduce lesions caused by cerebral ischaemia or excitotoxins by up to 70% or even more, and to reduce the amounts of beta-amyloid precursor protein (beta-APP) by 20% or more which are reduced by cerebral ischaemia.

The invention is illustrated but not limited by the following Examples and drawings.

EXAMPLE 1

Rats were treated to induce in them a stroke condition (a middle cerebral artery occlusion) by electro-cautery of the middle cerebral artery in the manner customary for such experimental study.

Male Sprague-Dawley rats (Charles River, U.K.) weighing 200–250 g were used in all experiments. The animals were injected icv (via previously implanted indwelling guide cannulae in the third ventricle of the brain), 10 minutes prior to surgery, with IL-1 ra (10 micrograms in 4 microlitres, i.e. 0.6 nmol, n=12, Synergen, Colo., USA) or 0.9% saline (4 microlitres, control, n=14 ), 30 minutes before and 10 minutes after surgery. Cerebral ischaemia was induced by permanent occlusion of the left middle cerebral artery (R. H. Lye et al., Neurosci.Meth. 22, 133, 1987) under halothane anaesthesia (2% in oxygen/nitrous oxide). All animals recovered consciousness within 10 minutes after completion of surgery and were allowed free access to food and water thereafter. The degree of damage, or protection against damage, was assessed by histological examination of the lesion size to assess the amount of non-viable tissue present. The data were summed from multiple experiments and derived from study of the rat brains 24 hours after the stroke condition commenced and also compared with control animals in which the treatment was not applied. The area of damage ($mm^2$) was assessed by tetrazolium staining on 500$\mu$ coronal sections of brain (area computed by Seescan image analysis).

The data summarised in FIG. 1 demonstrate that injection of this antagonist into the third ventricle of the brain 30 minutes before and 10 minutes after unilateral focal cerebral ischaemia (MCAo) in the rat inhibits neuronal damage (volume of infarct, measured 24 hours later) by approximately 50%.

In vehicle-treated ischaemic rats, histological damage (absence of mitochondrial respiratory activity) occurred reproducibly in basal ganglia and neocortex (FIG. 1). Injection of IL-1ra inhibited the extend of damage in these areas, reducing the total volume of the lesion from 84±12 $mm^3$ to 42±8 $mm^3$.

Our results therefore show that focal cerebral ischaemia is markedly inhibited (ca 50%) by cerebral injection of recombinant interleukin-1 receptor antagonist protein in the rat.

We have also shown effects of peripheral injection of recombinant interleukin-1 receptor antagonist protein ("IL-1 ra") on brain damage.

This was carried out by intravenous injection.

The IL-1 ra was given as a dose of 0.5 mg/kg., as a solution in normal saline.

This was administered as a first injection 30 minutes BEFORE the stroke, followed by a second injection 10 minutes AFTER the stroke.

|   | lesion size. |
|---|---|
| (1) after the above treatment | 57 ± 15 $mm^3$ |
| (2) control (no IL-1 ra) | 104 ± 14 $mm^3$ |

This may be expressed as being a 45% reduction in the size of the lesion or as a 45% protection against the effects of the stroke—a great clinical improvement.

EXAMPLE 2

Study of neuronal death resulting from focal cerebral ischaemia or excitotoxic damage due to striatal infusion of an NMDA-receptor agonist.

Figure 2:
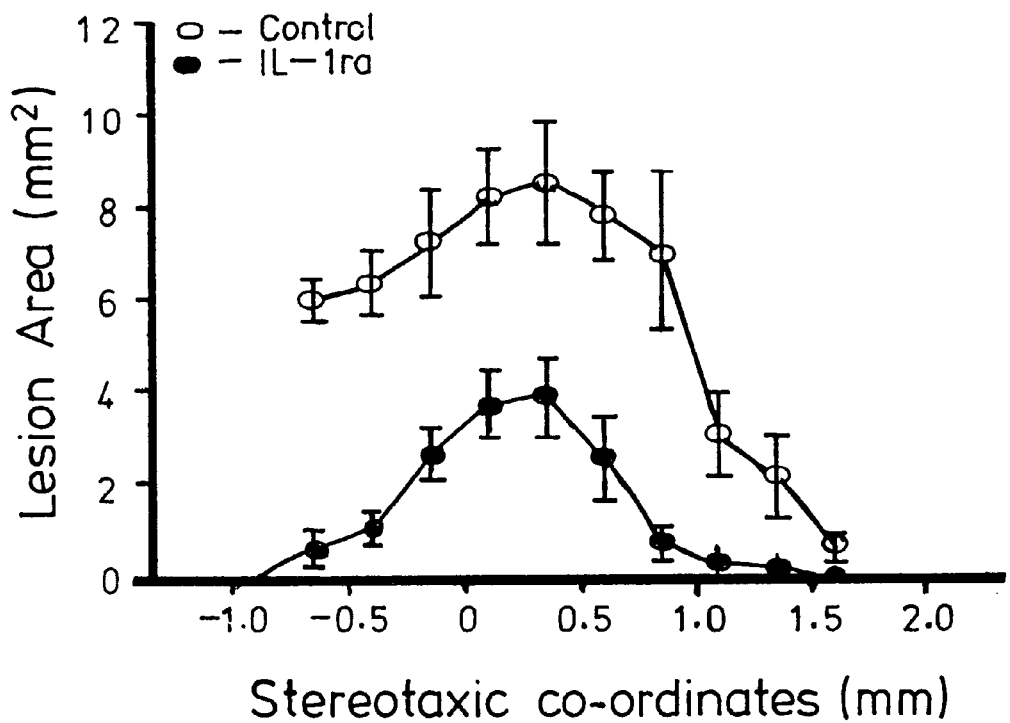
FIGS. 2A–B illustrate the effect of IL-1 receptor antagonist protein on NMDA receptor mediated neuronal damage. (A) Upper panel shows the area of damage ($mm^2$) and (B) the lower panel shows the lesion volume ($mm^3$, computed from the volume under the curve for upper panel). Mean±SEM, unpaired Students t-test, *$P<0.001$.
Figure 2:
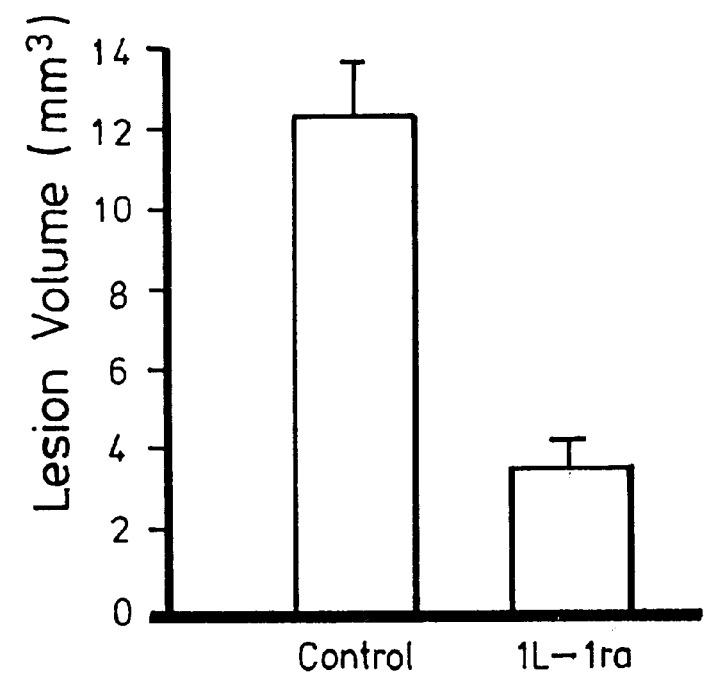

Excitatory amino acids are potent endogenous neurotoxic agents which can induce neuronal damage and have been proposed as mediators of neuronal death following ischaemia, mechanical brain injury, seizures or neurodegenerative conditions such as Parkinson's disease, Huntingdon's chorea and damage caused by infections such as HIV. The NMDA receptor has been strongly implicated in these excitotoxic actions of amino acids. Synthetic antagonists of NMDA receptors (e.g. MK801) are potent neuroprotective agents in ischaemia, while pharmacological NMDA receptor activation results in neuronal damage. Infusion of cis-2,4-methanoglutamate, a potent and selective NMDA agonist into the striatum of rats causes dose-dependent lesions which are markedly inhibited by pretreatment with MK801. Data presented in FIG. 2 show that infusion of 10 nmoles of cis-2,4-methanoglutamate caused reproducible lesions (12.3±1.3 $mm^3$, n=10). Infusion of the interleukin-1 receptor antagonist with the NMDA agonist significantly reduced the volume of lesions induced by the cis-2,4-methanoglutamate by 7.11±4.2%. This indicates that protection against excitotoxic damage is offered by the IL-1ra agonist.

We have also shown that brain damage caused by striatal infusion of quinolinic acid in rats is inhibited by IL-1ra. Quinolinic acid caused lesions (assessed from mitochondrial viability) of 27.8±2.4 $m^3$, coinfusion of IL-1ra (10 $\mu$g) reduced the size of the lesion to 15.1±2.7 $mm^3$ (i.e. by 46%). Quinolinic acid is a naturally occurring molecule which, when released in high quantities is toxic to neurons. Excess release of quinolinic acid has been reported in the brain in various neurological conditions (e.g. Huntingdon's chorea and AIDS) and may be a cause of neurological damage in these conditions. Therefore, inhibition of its actions by IL-1ra could be of benefit.

We have thus shown also that the IL-1ra fragment inhibits brain damage induced by administration of excitotoxic agents (NMDA receptor agonists or quinolinic acid) to rat brain. Since this mechanism of damage underlies many other neurological conditions (such as epileptic degeneration, Huntingdon's chorea, Parkinson's disease and brain damage resulting from infections such as HIV or traumatic brain injury) as well as ischaemic damage, the IL-ra may be of benefit in each of these conditions.

EXAMPLE 3

Methods

Rats (Sprague-Dawley 200–250 gms) were anaesthetized with halothane (2% in oxygen/nitrous oxide) and treated so as to induce a neurological lesion (an infarct). This was achieved by permanent occlusion of the left middle cerebral artery following an established procedure (Lye R H et al 1987 Neurosci. Meth. 22,133). The animals had previously been fitted with an indwelling guide cannula in the third ventricle in the brain and were injected with a solution of IL1-RA (10 micrograms in 4 microlitres i.e. 0.6 nmol) or 0.9% saline (4 microlitres) at intervals of 10 minutes and 30 minutes following the lesion procedure.

A total of 32 animals were used in the various experimental and control procedures.

Animals in treated and non-treated groups were examined after 24 hours (n=20 total) and 7 day (n=12 total) survival times.

The brain from each animal was fixed embedded in paraffin and processed for immunocytochemistry to assess the degree of immunoreactivity to β amyloid precursor protein in the brain (using both polyclonal and monoclonal antibodies to β amyloid precursor protein).

Results

Lesion size varied from animal to animal. However, increased immunoreactivity to the β amyloid precursor protein was consistently found in a region extending some 2 mm from the edge of the infarct. Animals treated with IL1-RA had a reduction in lesion size and also manifested a marked reduction of the levels of β amyloid protein precursor protein-immunoreactivity in the neurons surrounding the lesion.

Similar results were seen in animals with both 24 hour and 7 day survival times.

We claim:

1. A method of inhibiting or delaying neuronal cell death resulting from over-activation of NMDA receptors in the brain of a human being experiencing a condition of cerebral neurological degeneration arising from or related to cerebral ischaemia, comprising the step of administering to said human being in need of such treatment an effective amount of an agent wherein the agent is IL-1 ra.

2. The method of claim 1 wherein the IL-1 ra is recombinant IL-1 ra.

3. The method of claim 1 wherein the agent is a fragment of IL-1 ra.

4. The method of claim 1 wherein the agent is a synthetic IL-1 ra or fragment thereof.

5. The method of claim 1 wherein the agent is administered such that, at the site of action of the agent, the amount of the agent is between 100 and 10,000 micrograms per 80 kg body weight.

6. The method of claim 5 wherein the amount of the agent is between 1000 and 5000 micrograms per 80 kg body weight.

7. The method of claim 6 wherein the amount of the agent is about 2400 micrograms per 80 kg body weight.

8. The method of claim 1 wherein the agent is administered by injection.

9. The method of claim 1 wherein the agent is administered at a peripheral site from which it subsequently migrates within the body to the site of the identified or suspected neuro-degeneration.

10. The method of claim 9 wherein the agent is administered through the blood stream.

11. The method of claim 9 wherein the agent is administered by intravenous infusion.

12. The method of claim 1 wherein the agent is administered by transfer through the cerebro-spinal fluid.

13. The method of claim 1 wherein the agent is administered into the intra-cranial cavity.

14. The method of claim 1 wherein the agent is administered in a formulation in which it is dispersed or dissolved in a pharmaceutically acceptable carrier.

15. The method of claim 9 wherein the carrier is an aqueous medium.

16. The method of claim 15 wherein the aqueous medium is normal saline.

17. The method of claim 1 wherein the agent is administered continuously.

18. The method of claim 1 which is applied to a condition of cerebral neurological degeneration selected from the group consisting of a stroke, a haemorrhage and a brain injury resulting from trauma.

19. The method of claim 1 wherein the agent is administered after ischaemic damage has occurred or is suspected.

20. The method of claim 1 which is applied to excitotoxic brain damage.

21. A method of inhibiting or delaying neuronal cell death resulting from over-activation of NMDA receptors in the brain of a non-human mammal experiencing a condition of cerebral neurological degeneration arising from or related to cerebral ischaemia, comprising the step of administering to said mammal in need of such treatment an effective amount of an agent wherein the agent is IL-1 ra.

22. A method of inhibiting or delaying neuronal cell death resulting from over-activation of NMDA receptors in the brain of a human being, the method comprising administering to the human being in need of such treatment a therapeutically effective amount of an agent which inhibits the action of interleukin-1, wherein the active agent is IL-1ra.

* * * * *

UNITED STATES PATENT AND TRADEMARK OFFICE
CERTIFICATE OF CORRECTION

PATENT NO.   : 6,090,775
DATED        : July 18, 2000
INVENTOR(S)  : Rothwell

It is certified that error appears in the above-identified patent and that said Letters Patent is hereby corrected as shown below:

On title page, change

"[75] Inventors:   Nancy Jane Rothwell, Poulton-le-Fylde; Gareth Roberts, London, both of United Kingdom"

to read as:

--[75] Inventor:   Nancy Jane Rothwell, Poulton-le-Fylde; London, United Kingdom--

Signed and Sealed this

Twelfth Day of June, 2001

*Attest:*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO. : 6,090,775
DATED : July 18, 2000
INVENTOR(S) : Rothwell

It is certified that error appears in the above-identified patent and that said Letters Patent is hereby corrected as shown below:

<u>Title page,</u>
Change, "[75] Inventor: Nancy Jane Rothwell, Poulton-le-Fylde; London, United Kingdom"

to read as:

-- [75] Inventor: Nancy Jane Rothwell, Poulton-le-Fylde; United Kingdom --

This certificate supercedes Certificate of Correction issued June 12, 2001.

Signed and Sealed this

Eighteenth Day of June, 2002

*Attest:*

*Attesting Officer*

JAMES E. ROGAN
*Director of the United States Patent and Trademark Office*